United States Patent [19]
Sato et al.

[11] 3,993,839

[45] Nov. 23, 1976

[54] PRINTABILITY IMPROVERS FOR MOLDED SYNTHETIC RESIN PRODUCTS

[75] Inventors: Yasuhiko Sato; Akitoshi Komiya, both of Annaka, Japan

[73] Assignee: Shinetsu Chemical Company, Tokyo, Japan

[22] Filed: Jan. 15, 1975

[21] Appl. No.: 541,090

Related U.S. Application Data

[63] Continuation of Ser. No. 381,032, July 20, 1973, abandoned.

[30] Foreign Application Priority Data

July 24, 1972 Japan.............. 47-73948

[52] U.S. Cl................. 428/413; 428/446; 428/447; 428/520; 428/522; 428/523
[51] Int. Cl.²............... B32B 25/20; B32B 27/32; B32B 27/38
[58] Field of Search.......... 428/447, 446, 413, 510, 428/520, 522, 523

[56] References Cited
UNITED STATES PATENTS

| | | | |
|---|---|---|---|
| 2,716,656 | 8/1955 | Boyd | 260/429.5 |
| 2,751,314 | 6/1956 | Keil | 428/447 X |
| 3,013,993 | 12/1961 | Rust et al. | 260/2 |
| 3,014,826 | 12/1961 | Kohn et al. | 428/447 |
| 3,321,350 | 5/1967 | Fekete | 156/329 |
| 3,350,216 | 10/1967 | McVannel et al. | 428/447 |

OTHER PUBLICATIONS

Chemical Reviews, vol. 61, No. 1, Feb., 1961, "The Organic Chemistry of Titanium," Shiihara et al., pp. 1 and 19–30.

*Primary Examiner*—Harold Ansher
*Attorney, Agent, or Firm*—Toren, McGeady and Stanger

[57] ABSTRACT

Printability improving agents for molded synthetic resin products comprising organosiloxy titanic acid esters prepared by co-condensation of a titanic acid ester having the formula $Ti(OR^1)_4$ where $R^1$ is a monovalent hydrocarbon with a silane or siloxane compound having hydroxy or acetoxy radicals bonded to silicon atoms. Their solutions in an organic solvent are applied to surfaces of molded silicone rubber, polyester or other synthetic resin products in order to make the treated surfaces far more printable with or acceptable to various inks and, as a result, the printed ink will be safe from abrasion.

11 Claims, No Drawings

PRINTABILITY IMPROVERS FOR MOLDED SYNTHETIC RESIN PRODUCTS

CROSS-REFERENCE TO RELATED APPLICATIONS

This is a continuation of application Ser. No. 381,032 filed July 20, 1973, now abandoned.

FIELD OF THE INVENTION

This invention relates to printability improvers, or compositions which are applied on surfaces to be printed of molded synthetic resin products, particularly of silicone products, to improve their printability, such improvers containing as the main component, organosiloxy titanic acid esters.

DESCRIPTION OF THE PRIOR ART

Various synthetic resins, especially silicones, have desirable properties, including good resistance to heat and water as well as excellent flame retardancy and electrical properties, and they are useful in a wide variety of industries, particularly in connection with sealing on semiconductor products, such as, diodes, transistors, thyristors and integrated circuits, and molding or extrusion to electrical appliance parts, such as, connectors, bushings and switches. Those molded products, however, have smooth and inactive surfaces so that it is difficult to print on them, for example, trade marks and names of the article and the manufacturer. And yet, even if it is done, the printed ink is apt to come off or become faded during transportation and application. In the case where they are used for the semiconductor parts, they have to be washed with solvents before being assembled, possibly resulting in the disappearance of the printed images.

In order to overcome the above difficulties and drawbacks, several methods have been proposed: for example, to have the surfaces of the molded products on which the printing ink should be transferred, roughened by means of a blast with crushed nuts or glass beads; washing the surfaces of molded products with an organic solvent, such as, trichloroethylene, rubber solvent, methylchloroform, toluene, methylguanidine and Uresolveplus (trademark used by Dianloy Incorp.) so that they may be slightly dissolved, and applying various surface-treating agents on the surfaces of the molded products. But none of the methods have been successful; In each case, the printed ink was easily removed by rubbing, or, even if the printed ink stayed, it was easily rubbed off by dipping the image area in an organic solvent and then slightly rubbing it, for example, with gauze.

SUMMARY OF THE INVENTION

It is an object of the invention to provide a printability improver for molded synthetic resin products, free from the above-described disadvantages.

It is another object of the invention to improve the printability or ink transfer on the surfaces of various synthetic resin products molded of various synthetic resins.

It is a further object of the invention to provide the surfaces of various synthetic resin products with conditions suitable for printing or ink transfer, and which are safe from abrasion and solvent-washability problems.

The printability improver of the invention is a composition comprising, as the main component, an organosiloxy titanic acid ester having the average formula $$(R^1O)_{4-n}Ti(OSiR^2R^3R^4)_n$$

where $R^1$ is a monovalent hydrocarbon radical having from 1 to 18 carbon atoms; $R^2$, $R^3$ and $R^4$ are the same or different monovalent organic radicals selected from the group consisting of monovalent hydrocarbon radicals having from 1 to 6 carbon atoms and organosiloxy radicals having the average formula $$(R^5)_a SiO_{4-a/2}$$

where $R^5$ is the same or different monovalent organic radicals selected from the group consisting of hydrocarbon and alkoxy radicals having from 1 to 6 carbon atoms and $a$ is a positive number of from 1.5 to 3; and $n$ is a number of from 0.3 to 3.2.

This invention is based on the observation that printing or stamping with various inks can be carried out very easily on the surfaces of products molded of synthetic resins, particularly, of silicones, which have been treated with the above-given organosiloxy titanic acid ester and that the printed or stamped ink can hardly be removed.

Referring to the above-mentioned formula representing and defining the organosiloxy titanic acid esters of the invention, it is required so as to advantageously attain the objects of the invention that the average value of n should be in the range of from 0.3 to 3.2, preferably from 0.4 to 2.5, for, if it is out of the range, their effect of improving the printability would be reduced. The monovalent hydrocarbon radicals having from 1 to 18 carbon atoms, denoted by $R^1$ in the same formula, are exemplified by methyl, ethyl, n-propyl, iso-propyl, tert-butyl, octyl and phenyl radicals. The monovalent hydrocarbon radicals having from 1 to 6 carbon atoms denoted by $R^2$, $R^3$, $R^4$ and $R^5$ in the abovementioned formulas are exemplified by methyl, ethyl, n-propyl, iso-propyl, tert-butyl, phenyl, vinyl, allyl, triorganosiloxy, and polyorganosiloxy radicals.

The organosiloxy titanic acid esters can be prepared by a variety of known methods. One example of the methods is co-condensation of a titanic acid ester, such as tetra(tert-butyl)titanic acid ester, tetra(isopropyl)titanic acid ester, tetra(stearyl)titanic acid ester, or tetra(phenyl)titanic acid ester, with an organic silicone compound, such as, dimethyl vinyl silanol, dimethyl phenyl silanol, trimethyl acetoxy silane, tripropyl acetoxy silane, methyl phenyl siloxane, methyl vinyl siloxane, methyl phenyl methoxy siloxane, or methyl vinyl methoxy siloxane.

The above-mentioned co-condensation may be conducted in accordance with the manners as proposed by D. C. Bradley et al in Chemistry and Industry (London), 1958, page 1231. That is to say, a titanic acid ester having the formula $Ti(OR^1)_4$ is added into an organic solvent, and to this solution, while being heated and refluxed, is added a silane or siloxane having hydroxy or acetoxy radicals bonded to silicon atoms for co-condensation reaction. The organic solvent used is an aromatic hydrocarbon, such as, benzene, toluene or xylene, an aliphatic hydrocarbon, such as, n-hexane or cyclohexane, or a chlorinated hydrocarbon such as trichloroethylene. During the co-condensation reaction, the azeotrope of the solvent and alcohol or acetate produced is removed out of the reaction system, to further proceed with the co-condensation.

The printability improver of the present invention which comprises the organosiloxy titanic acid ester may be made into a 5–30% solution with a known organic solvent selected from the group consisting of toluene, xylene, trichloroethylene and aliphatic hydrocarbon, so that it may be applied to various surfaces by means of known brushing, dipping or spraying methods. The amount of the improver applied may be such that the cured film is only several microns thick. After the application, it may be dried either naturally or in hot blast. The treated surfaces are thus provided with excellent receptivity to the usual printing inks of epoxy, polyester or alkyd resins, and also the ability to prevent the printed ink from becoming thin or disappearing.

The synthetic resins of which the products to which the printability improvers of the present invention can suitably be applied include, besides silicone resins and rubbers, resins of polyester, phenol, epoxy and acryl, as well as polyvinyl chloride, polyethylene and polystyrene.

There follow a number of illustrative examples.

EXAMPLE 1.

One mole of $CH_3(C_6H_5)_2SiH$ (214 g) in 100 cc cyclohexane was added dropwise during 4 hours to a boiling solution of 1 mole of $Ti(OC_2H_5)_4$ (228 g) in 300 cc cyclohexane. The azeotrope of cyclohexaneethyl acetate was collected by fractional distillation. After the reaction was complete, the solvent was removed by evaporation in vacuo and 0.9 mole of $Ti[OSi(C_6H_5)_2\text{-}CH_3][OC_2H_5]_3$ (357 g, 90% yield) was obtained as residue. The thus obtained co-condensate, methyldiphenylsiloxy-triethyl titanic acid ester, was dissolved in toluene to make a 10% solution. This solution was applied on the surface of a product molded of slicone resin by means of brush coating and was allowed to stand for 5 minutes. On the thus treated surface was made printing with ink from alkyd resin, and the printed surface was dried by hot blast at 120° C for 15 minutes. The dried surface was slightly rubbed by a piece of gauze impregnated with toluene, resulting in no peeling off of the printed ink.

For comparison purposes, similar printing was carried out on the surface which had not been treated with the solution of the methyldiphenylsiloxy-triethyl titanic acid ester in toluene but washed with toluene alone. Slight rub of such surface with toluene-impregnated gauze resulted in the disappearance of the printed ink almost in its entirety.

EXAMPLE 2.

The various titanic acid esters and organic silicone compounds in the mole ratios as set forth in Table I following were co-condensated, and the resulting 7 co-condensates were subjected to subsequent procedures of application and printing were carried out similarly to Example 1. Thereafter, the printed surfaces were tested by 2 different tests, (1) and (2), in order to determine their conditions. The results are also shown in the table.

In Table I are shown also Comparative Examples 1 and 2, where the surfaces were not coated with the organosiloxy titanic acid ester but merely treated with No. 400 sand paper and immersed in Uresolveplus (solvent, trademark used by Dianloy Incorp.) for 10 minutes, respectively, prior to printing, and the results of tests similar to the above-mentioned Tests (1) and (2).

The ink used in Example 2 and Comparative Examples 1 and 2 is varied by 3 groups, i.e., of epoxy, polyester and alkyd resins, as denoted by A, B and C, respectively, in the table.

Test (1) was conducted by rubbing the printed surface 10 times with a piece of gauze, while Test (2) by rubbing the printed surface which had been immersed in trichloroethylene for 10 minutes. In both tests, the resulting conditions on the surface were observed and the results are set forth in the table by 3 classes of "o", "Δ" and "x", mark o denoting no change to the printed ink, mark Δ denoting about half of the printed ink removed, and mark x, almost all of the printed ink removed.

TABLE I

| No. | Organic silicone compound | Titanic acid ester | n* | Ink | Test (1) | Test (2) |
|---|---|---|---|---|---|---|
| 1 | Dimethylvinyl silanol (1.5 mol) | Tetrabutyl titanic acid ester (1 mol) | 1.5 | A<br>B<br>C | o<br>o<br>o | o<br>Δ<br>Δ |
| 2 | Dimethylphenyl silanol (1 mol) | Tetraisopropyl titanic acid ester (1 mol) | 1.0 | A<br>B<br>C | o<br>o<br>o | o<br>Δ<br>Δ |
| 3 | Tripropylsilyl acetate (0.4 mol) | Tetrastearyl titanic acid ester (1 mol) | 0.4 | A<br>B<br>C | o<br>o<br>Δ | o<br>Δ<br>Δ |
| 4 | Trimethylsilyl acetate (0.3 mol) | Tetraisopropyl titanic acid ester (1 mol) | 0.3 | A<br>B<br>C | o<br>Δ<br>Δ | o<br>Δ<br>Δ |
| 5 | Trimethylsilyl acetate (0.6 mol) Dimethylvinyl-silyl acetate (0.6 mol) | Tetraphenyl titanic acid ester (1 mol) | 1.2 | A<br>B<br>C | o<br>o<br>o | o<br>o<br>o |
| 6 | Trimethylsilyl acetate (0.4 mol) Methylphenyl-methoxy siloxane (0.4 mol) Methylvinyl-methoxy siloxane (0.6 mol) | Tetrabutyl titanic acid ester (1 mol) | 1.4 | A<br>B<br>C | o<br>o<br>o | o<br>o<br>o |
| 7 | Trimethylacetoxy silane (2.4 mol) | Tetraisopropyl titanic acid ester (1 mol) | 2.4 | A<br>B<br>C | o<br>o<br>o | o<br>Δ<br>Δ |
| COMPARATIVE EXAMPLE | | | | | | |
| 1 | The surface of the molded product was ground with No. 400 sand paper. | | | A<br>B<br>C | Δ<br>x<br>x | Δ<br>x<br>x |
| 2 | The molded product was immersed in Uresolveplus for 10 min. | | | A<br>B<br>C | o<br>x<br>x | Δ<br>x<br>x |

Note: *n is in reference with the average formula representing the organosiloxy titanic acid ester $(R^1O)_{4-n}Ti(OSiR^2R^3R^4)_n$.

EXAMPLE 3

The varied kinds of organosiloxy titanic acid ester were applied to products molded of silicone rubber and epoxy and polyethylene resins as set forth in Table II following. Printing was made on the surface of each product with ink A, B or C, as referred to in the description of Example 2 and, thereupon, the printed surfaces were subjected to tests (1') and (2') similar to those of Example 2. The details and results of the tests are shown in the table.

TABLE II

| Product molded of: | Organosiloxy titanic acid ester | Ink | Test (1') | Test (2') |
|---|---|---|---|---|
| Silicone rubber | Not used | A<br>B<br>C | Δ<br>x<br>x | Δ<br>x<br>x |
| | i | A<br>B | o<br>o | o<br>Δ |

TABLE II-continued

| Product molded of: | Organosiloxy titanic acid ester | Ink | Test (1') | Test (2') |
|---|---|---|---|---|
| | | C | o | Δ |
| | 6 | A | o | o |
| | | B | o | o |
| | | C | o | Δ |
| Epoxy resin | Not used | B | o | Δ |
| | | C | o | Δ |
| | 2 | B | o | o |
| | | C | o | o |
| | 5 | B | o | o |
| | | C | o | o |
| Polyethylene resin | | A | o | Δ |
| | Not used | B | Δ | x |
| | | C | Δ | x |
| | 1 | A | o | o |
| | | B | o | o |
| | | C | o | Δ |
| | 3 | A | o | o |
| | | B | o | o |
| | | C | o | Δ |

What is claimed is:

1. A molded synthetic resin article having a layer of an organosiloxy titanic acid ester having the average formula

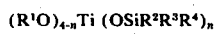

where $R^1$ is a monovalent hydrocarbon radical having from 1 to 18 carbon atoms; $R^2$, $R^3$ and $R^4$ are the same or different monovalent organic radicals selected from the group consisting of monovalent hydrocarbon radicals having from 1 to 6 carbon atoms and organosiloxy radicals having the average formula

where $R^5$ is the same or different monovalent organic radicals selected from the group consisting of hydrocarbon and alkoxy radicals having from 1 to 6 carbon atoms and a is a positive number of from 1.5 to 3; and n is a number of from 0.3 to 3.2.

2. The article of claim 1 wherein n is from 0.4 to 2.5.
3. The article of claim 1 wherein said molded synthetic resin products are made of silicone resins and rubbers, epoxy resins and polyethylene.
4. The article of claim 1 wherein said organosiloxy titanic acid ester is $Ti[OSi(C_6H_5)_2CH_3][OC_2H_5]_3$.
5. The article of claim 1 wherein said organosiloxy titanic acid ester is a compound prepared by co-condensation of dimethylvinyl silanol with tetrabutyl titanic acid ester.
6. The article of claim 1 wherein said organosiloxy titanic acid ester is a compound prepared by co-condensation of dimethylphenyl silanol with tetraisopropyl titanic acid ester.
7. The article of claim 1 wherein said organosiloxy titanic acid ester is a compound prepared by co-condensation of tripropylsilyl acetate with tetrastearyl titanic acid ester.
8. The article of claim 1 wherein said organosiloxy titanic acid ester is a compound prepared by co-condensation of trimethylsilyl acetate with tetraisopropyl titanic acid ester.
9. The article of claim 1 wherein said organosiloxy titanic acid ester is a compound prepared by co-condensation of trimethylsilyl acetate and dimethylvinylsilyl acetate, on one part, with tetraphenyl titanic acid ester, on the other part.
10. The article of claim 1 wherein said organosiloxy titanic acid ester is a compound prepared by co-condensation of trimethylsilyl acetate, methylphenylmethoxy siloxane and methylvinylmethoxy siloxane, on one part, with tetrabutyl titanic acid ester, on the other part.
11. The article of claim 1 wherein said organosiloxy titanic acid ester is a compound prepared by co-condensation of trimethylacetoxy silane with tetraisopropyl titanic acid ester.

* * * * *